(12) United States Patent
Baker et al.

(10) Patent No.: US 7,691,139 B2
(45) Date of Patent: Apr. 6, 2010

(54) UNIDIRECTIONAL DELIVERY SYSTEM

(75) Inventors: Deborah A. Baker, Lafayette, IN (US);
James D. Purdy, Lafayette, IN (US);
Fred T. Parker, Unionville, IN (US)

(73) Assignee: Cook Incorporated, Bloomington, IN (US)

( * ) Notice: Subject to any disclaimer, the term of this patent is extended or adjusted under 35 U.S.C. 154(b) by 841 days.

(21) Appl. No.: 11/318,690

(22) Filed: Dec. 27, 2005

(65) Prior Publication Data

US 2006/0190069 A1   Aug. 24, 2006

Related U.S. Application Data

(60) Provisional application No. 60/639,671, filed on Dec. 28, 2004.

(51) Int. Cl.
*A61F 2/84* (2006.01)
(52) U.S. Cl. ..................................... 623/1.11
(58) Field of Classification Search ............... 623/1.11, 623/1.12, 1.16, 1.25, 1.27, 2.11; 606/108, 606/194; 604/164.01, 164.12, 264
See application file for complete search history.

(56) References Cited

U.S. PATENT DOCUMENTS

| | | | | |
|---|---|---|---|---|
| 4,665,918 A | * | 5/1987 | Garza et al. | 606/108 |
| 5,571,168 A | * | 11/1996 | Toro | 623/1.11 |
| 5,733,267 A | * | 3/1998 | Del Toro | 623/1.11 |
| 6,190,360 B1 | * | 2/2001 | Iancea et al. | 604/164.09 |
| 6,709,454 B1 | | 3/2004 | Cox et al. | |
| 6,849,084 B2 | | 2/2005 | Rabkin et al. | 623/1.12 |
| 6,939,370 B2 | | 9/2005 | Hartley et al. | |
| 2001/0047150 A1 | | 11/2001 | Chobotov | 604/107 |
| 2001/0051822 A1 | * | 12/2001 | Stack et al. | 623/1.11 |
| 2004/0127912 A1 | | 7/2004 | Rabkin et al. | 606/108 |
| 2005/0027345 A1 | | 2/2005 | Horan et al. | 623/1.12 |

FOREIGN PATENT DOCUMENTS

EP   0 696 447 B1   2/1996

* cited by examiner

*Primary Examiner*—Anhtuan T Nguyen
*Assistant Examiner*—Ryan J Severson
(74) *Attorney, Agent, or Firm*—Brinks Hofer Gilson & Lione

(57) ABSTRACT

A tubular prosthesis delivery system has an inner tubular member having a distal end including a prosthesis-carrying portion and a proximal end intended to remain outside the patient. An outer tubular member has a distal end spaced from the prosthesis-carrying portion of the inner member. A coupling member couples the inner and outer tubular members to each other in fixed relationship generally at a location intended to remain outside the patient. An intermediate tubular member located between the inner and outer tubular members has a distal end adapted to cover the tubular prosthesis and a proximal end that projects proximally beyond the proximal ends of both the inner and outer tubular members. The proximally projecting end of the intermediate tubular member is longitudinally movable with respect to the coupled inner and outer tubular members by a distance sufficient to retract the intermediate tubular member distal end from any position covering the prosthesis carried by the inner member.

21 Claims, 6 Drawing Sheets

UNIDIRECTIONAL DELIVERY SYSTEM

CROSS-REFERENCE TO RELATED APPLICATIONS

This application is related to and claims all benefits of U.S. Provisional Application Ser. No. 60/639,671 filed Dec. 28, 2004, which is hereby incorporated by reference.

BACKGROUND

1. Technical Field

This invention relates to a medical device delivery system. The medical device delivery system has a host of uses including as a stent delivery catheter system. The delivery system employs a retractable sheath which exposes a medical device for deployment.

2. General Background

Stents and delivery systems for deploying stents are highly developed and constitute a well known field of medical technology. Stents have many well known uses and applications. A stent is a prosthesis which is generally tubular and which is expanded radially in a vessel or lumen to repair dissection, prevent restenosis, or otherwise maintain its patency. Stents are widely used in body vessels, body canals, ducts or other body lumens. For the purposes of this disclosure stents and medical devices may be considered to include any stent, covered stent, stent-graft, or other generally tubular expandable prosthesis intended for placement within a lumen of a patient.

A stent may either be self-expanding or balloon expandable. For the latter type, the stent is often delivered on a balloon and the balloon is used to expand the stent. The self-expanding stents may be made of shape memory materials such as nitinol or constructed of other metals but of a design which exhibits self expansion characteristics. Stents, stent-grafts and the like are commonly delivered using a catheter delivery system. In most stent delivery systems, the stent, and the balloon if present, are held down and covered by a sheath or sleeve that extends over the stent and may extend over a substantial portion of the catheter. When the stent is suitably positioned at its desired location within the targeted vessel, the sheath or sleeve is retracted, generally in a proximal direction on the catheter, to expose the stent. When the sheath is removed, the stent is free to self-expand or be expanded with the balloon.

Throughout this specification the term proximal is used in the convention manner for that end of both the deployment device and the stent graft which is closer to the physician or other professional manipulating the device, and the term distal is used for that end of the deployment device or stent graft which in use is furthest from the physician.

A known delivery system for delivering a self-expanding stent is disclosed in U.S. Pat. No. 6,939,370. This known delivery system has a distal end adapted to be introduced into a patient and a proximal end including a handle arrangement adapted to remain outside a patient. The delivery system includes two catheters which are concentrically arranged. A nose cone dilator is positioned at the distal end of the inner catheter. The two catheters are designed to be inserted into a patient over a guide wire. The stent is carried axially around the distal end of the inner catheter. The catheter distal end has a region adapted in use to contain a stent graft. The outer catheter forms a sheath arrangement that initially extends over and covers the region containing the stent graft. The stent is carried to the delivery site while being held in a compressed delivery configuration by the outer catheter or sheath. The sheath is adapted to be moved with respect to the inner catheter by movement of the handle arrangement to expose the region containing the stent, thereby enabling deployment of the stent at the delivery site.

The handle arrangement of this known delivery system generally includes a fixed handle and a sliding handle. The sheath is fixed to the sliding handle sheath manipulator, whereby movement of the sheath manipulator with respect to the fixed handle moves the sheath independent of movement of the nose cone dilator. The sheath manipulator is located toward the distal end of the fixed handle and is adapted to slide proximally with respect to the handle to move the sheath so as to expose the region containing the stent. The distal location of the sheath manipulator is found by some physicians to be somewhat awkward to the point that such physicians occasionally move the fixed handle distally while moving the sheath manipulator proximally, thus causing the stent to expand at an untended site that is distal from the intended site. Some attempts have been made to provide a stent delivery system that provides the physician with a more easily manipulated handle mechanism that will reduce the potential for movement of the portion of the catheter carrying the stent during sheath retraction.

U.S. Pat. No. 5,733,267 discloses a pull back stent delivery system that has three concentric catheters with an inner catheter carrying a medical device such as a stent. A middle pull back catheter or sheath and an outer stiffening catheter surround the inner catheter. The inner and outer catheters are connected together at the handle end of the delivery system by a manifold stabilizer in an attempt to preclude the inner catheter from moving axially as the middle pull back catheter or sheath is retracted to provide for more accurate placement of the medical device. The manipulating handle for the middle pull back sheath is located between the ends of the manifold stabilizer. Movement of the manipulating handle for the middle pull back sheath is more controlled but a counter movement of the manifold stabilizer can still be experienced.

U.S. Pat. No. 6,709,454 discloses a stent delivery system that includes three concentric catheters with the inner and outer catheters coupled to a housing assembly which provides a manual mechanism for retracting the restraining sheath located between the inner and outer catheters. The housing assembly is designed to substantially immobilize the inner catheter, preventing it from moving relative to the restraining sheath during stent deployment. The housing assembly includes a curved base which has a contour which conforms to the patient's leg. The design of the housing tends to cause the physician to push down on the housing assembly during deployment rather than forward. This downward pressure inhibits the inner tubular member assembly from moving forward toward the patient. The design is one that allows the system to be operated by just one hand, freeing the physician's other hand for other purposes, such as stabilizing the guiding catheter during stent deployment. The sheath is coupled to a pull-back handle located in the middle of the base that is intended to be operated by the index and middle finger of the physician. The one-handed movement of this handle can still cause some undesirable forward movement of the inner tubular member.

What is still needed is a stent deployment system wherein the handle connected to the covering sheath is situated at the end of the handle nearest the physician so that movement of that handle is achieved by merely a rearward pulling movement that is not inhibited by any adjacent portion of a handle or base.

BRIEF SUMMARY

A delivery system of the present invention is designed for the placement of a tubular prosthesis at a selected location within a lumen of a patient. The delivery system includes an inner tubular member having a distal end including a portion intended to carry a tubular prosthesis, and a proximal end intended to remain outside the patient. An outer tubular member surrounds the inner tubular member and has a distal end that is spaced from the inner member proximal end so that a projecting portion of the inner member carrying the tubular prosthesis projects distally beyond the outer member distal end. A coupling member couples the inner and outer tubular members to each other in fixed relationship generally at a location intended to remain outside the patient. An intermediate tubular member is located between the inner and outer tubular members. The intermediate tubular member has a distal end adapted to cover the tubular prosthesis carried by the inner member projecting portion. The intermediate tubular member also has a proximal end that projects proximally beyond the proximal ends of both the inner and outer tubular members. The proximally projecting end of the intermediate tubular member is longitudinally movable with respect to the coupled inner and outer tubular members by a distance sufficient to retract the intermediate tubular member distal end from any position covering the inner member projecting portion and any prosthesis carried thereby.

A proximal portion of the intermediate tubular member can include one or more longitudinal slots. The coupling member can extend through the longitudinal slot to couple the inner and outer tubular members to each other. The coupling member is longitudinally shorter than the longitudinal slot so that the intermediate tubular member is longitudinally movable with respect to the coupled inner and outer tubular members. The intermediate tubular member is movable by proximal movement of the proximal end that projects beyond the proximal ends of both the inner and outer tubular members. The length of the longitudinal slot is sufficient to permit movement of the intermediate tubular member by a distance sufficient to retract the intermediate tubular member distal end from any position covering any prosthesis carried by the inner member projecting portion.

The coupling member can take the form of one or more outwardly extending or flaring projections from the inner tubular member, each outward projection having an outer end coupled to the outer tubular member. The outward projections can be sufficiently flexible to permit initial assembly of the delivery system by inward radial collapse of the outward projections until aligned within the longitudinal slots in the intermediate tubular member. The outer end of each outward projection can be received in a recess in the outer tubular member. The outer end of each outward projection can be bonded to the outer tubular member.

A proximal portion of the outer tubular member can take the form of a handle that can include one or more ports for admitting fluids into the interior of one or more of the tubular members. A fluid port can be included to admit a fluid to force expansion of a balloon located within the inner member projecting portion to expand a balloon-expandable stent. One or more release mechanisms can be movably located at the proximal end of the outer tubular member to regulate the release one or more ends of the stent carried by the inner member projecting portion. Suitable seals can be included in the handle to prevent loss of fluids from the proximal end of the delivery system.

Additional features and advantages of a delivery system of the present invention will become apparent from the illustrative examples shown in the accompanying drawings. The components in the Figures are not necessarily to scale, emphasis instead being placed upon illustrating the principles of the invention. Moreover, in the Figures, like referenced numerals designate corresponding parts throughout the different views.

DESCRIPTION OF THE PREFERRED EMBODIMENTS

Figure 1:
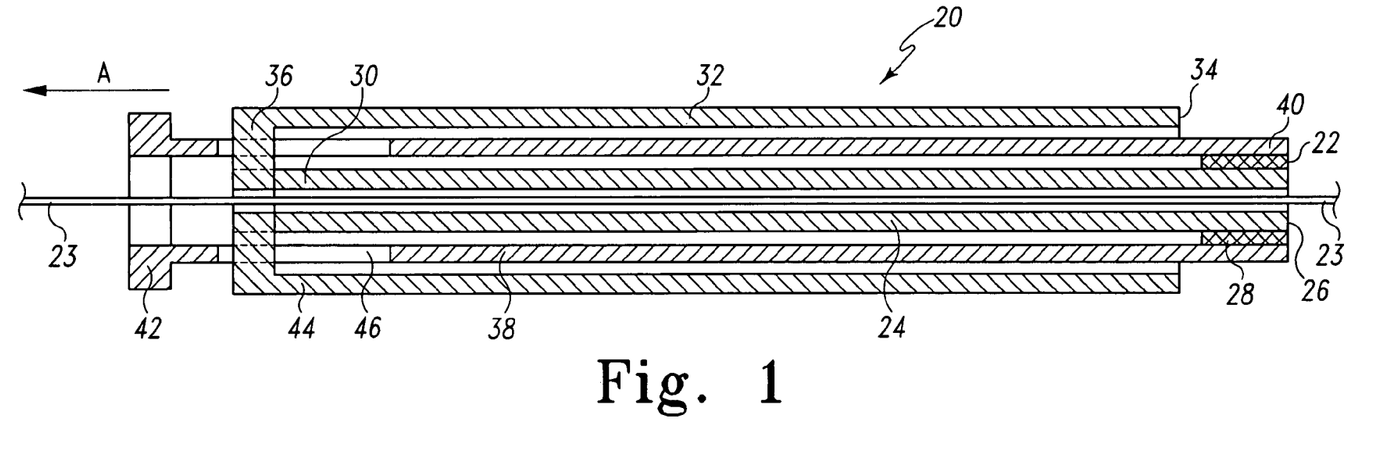
FIG. 1 is a diagrammatic view of a prosthesis deployment system of the present invention in an insertion and location attitude with the prosthesis in a retained position.
Figure 2:
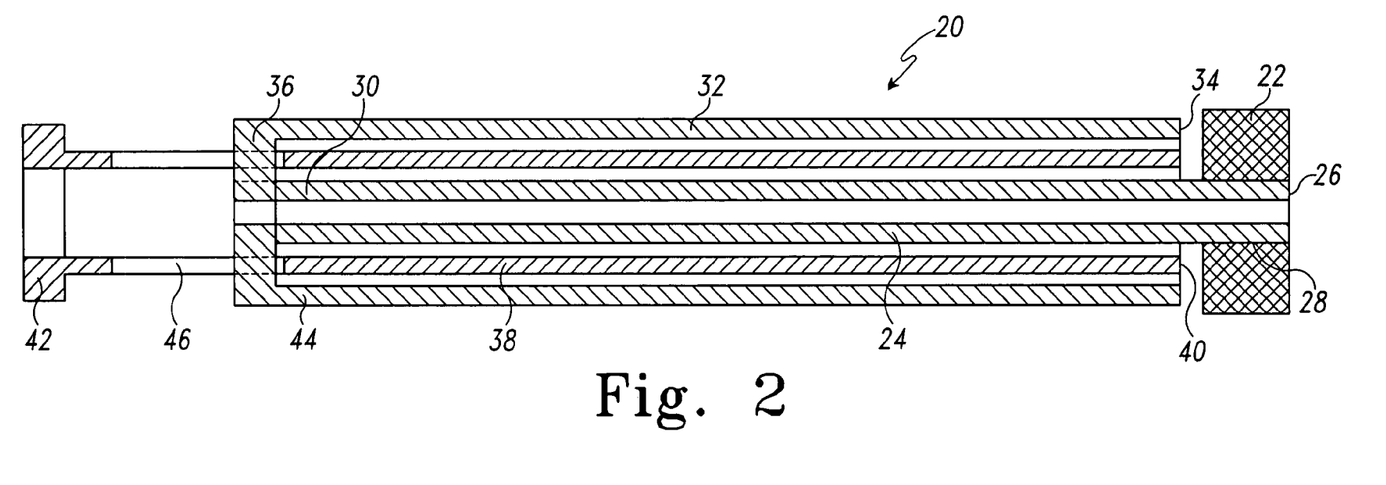
FIG. 2 is a diagrammatic view of the prosthesis deployment system shown in FIG. 1 in a deployment and withdrawal attitude with the prosthesis in an expanded position.

A schematic presentation of a delivery system 20 of the present invention is shown in FIGS. 1 and 2. The delivery system 20 is designed to place a tubular prosthesis 22 at a selected location within a lumen of a patient, not shown. This placement can be accomplished with the aid of a guide wire 23 shown in FIG. 1. The tubular prosthesis 22 can be a stent, a stent-graft, a vascular graft, an infusion sleeve, a shunt, or any number of other implantable medical devices intended for temporary or permanent placement within a lumen of a patient. The use of the term prosthesis or stent in this disclosure is not intended to be limiting, but merely exemplary of one possible use of the delivery system 20. The delivery system 20 includes an inner tubular member 24 having a distal end 26 including a portion 28 intended to carry a tubular prosthesis 22. The inner tubular member 24 also has a proximal end 30 intended to remain outside the patient. An outer tubular member 32 surrounds the inner tubular member 24. The outer tubular member 32 has a distal end 34 that is spaced from the distal end 26 of the inner member 24 so that the projecting portion 28 of the inner member 24 carrying the tubular prosthesis 22 projects proximally beyond the outer member distal end 34. A coupling member 36 couples the inner tubular member 24 to the outer tubular member 32 to fix the positional relationship between the two members 24 and 32. The coupling member 36 is generally at a location intended to remain outside the patient, and can be situated at or adjacent to the proximal end 44 of outer tubular member 32 and the proximal end 30 of the inner tubular member 24.

An intermediate tubular member 38 is located between the inner tubular member 24 and outer tubular member 32. The intermediate tubular member 38 has a distal end 40 adapted to cover the tubular prosthesis 22 carried by the projecting portion 28 of the inner member 24. The intermediate tubular member 38 also has a proximal end 42 that projects proximally beyond the proximal ends 30, 44 of both the inner and outer tubular members 24, 32. The proximally projecting end 42 of the intermediate tubular member 38 can be enlarged to permit easy grasping. The proximally projecting end 42 is movable longitudinally with respect to the coupled inner and outer tubular members 24, 32 in the direction of arrow A as illustrated by the difference between FIGS. 1 and 2. Any longitudinal movement of the proximally projecting end 42 necessarily also causes a similar movement by the remainder of the intermediate tubular member 38 including the distal end 40 adapted to cover the tubular prosthesis 22 carried by the projecting portion 28 of the inner member 24. The intermediate tubular member 38 is designed to be longitudinally moved by a distance sufficient to retract the distal end 40 from any position covering the prosthesis 22 carried by the projecting portion 28 of the inner member 24, thus permitting the prosthesis 22 to expand as shown in FIG. 2. The regulation of this movement can be achieved by having the coupling member 36 pass through a slot 46 in the intermediate tubular member 38. The length of the slot 46 regulates the length of longitudinal movement of the intermediate tubular member 38.

Figure 3:
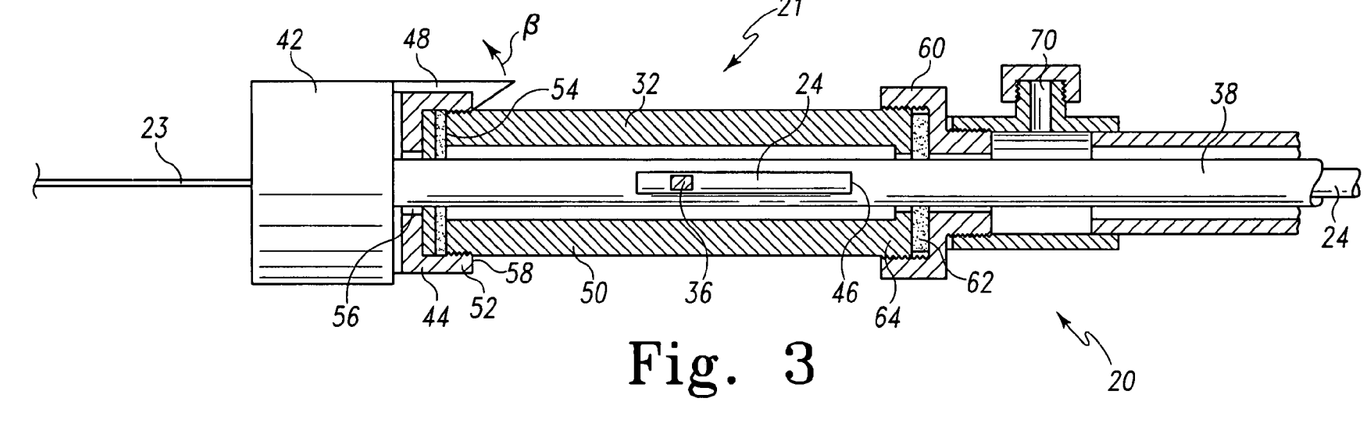
FIG. 3 is a side elevation view partially in section of the handle portion of a directional system of the present invention situated in an insertion and location attitude.
Figure 4:
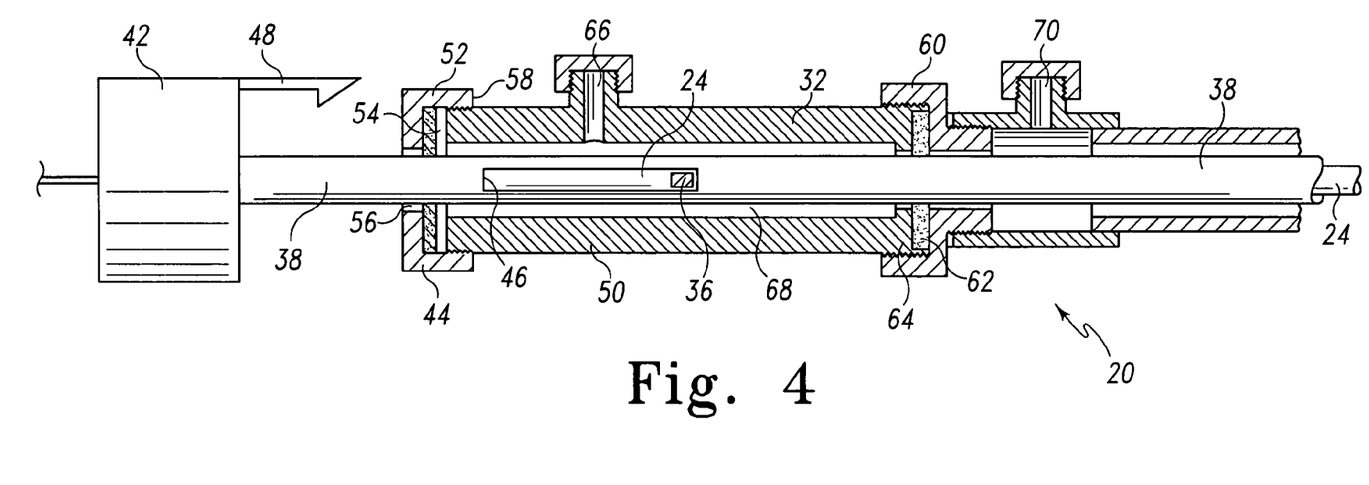
FIG. 4 is a side elevation view similar to FIG. 3 with the handle portion moved to the deployment and withdrawal attitude.

The proximal end portion 21 of a practical embodiment of a delivery system 20 of the present invention is shown in FIG. 3 in a position approximately reproducing the position of the system shown in FIG. 1. A minor variation of the delivery system 20 of FIG. 3 is shown in FIG. 4 in a position approximately reproducing the position of the system shown in FIG. 2. The inner tubular member 24 is seen to be projecting to the right beyond a right end schematic termination of the intermediate tubular member 38. The inner tubular member 24 surrounds the guide wire 23, when present. The inner tubular member 24 can also be seen through the slot 46 in the intermediate tubular member 38. The coupling member 36 can also be seen, in section, extending through the slot 46 from the inner tubular member 24 outward to the outer tubular member 32. The intermediate tubular member 38 is seen to include an enlarged proximal end 42 having a latch 48 that is intended to interact with the proximal end 44 of the outer tubular member 32.

The proximal end 44 of the outer tubular member 32 is seen in FIGS. 3 and 4 to include a tubular handle portion 50 having a proximal end cap 52. The proximal end cap 52 can secure one or more seals 54 to the end of the tubular handle portion 50. The seals 54 surround the intermediate tubular member 38 to inhibit fluid leakage out of the central opening 56 in the proximal end cap 52. The proximal end cap 52 also has a forward facing edge 58 that can cooperate with latch 48 to ensure that no relative movement between the outer tubular member 32 and the intermediate tubular member 38 takes place until the latch 48 is released by movement in the direction of arrow B. A distal end cap 60 can secure another seal 62 to the distal end 64 of the tubular handle portion 50.

A port 66 can be provided that leads to the interior chamber 68 within the tubular handle portion 50. The port 66 and chamber 68 can provide fluid access via the longitudinal slot 46 to the space between the inner tubular member 24 and the intermediate tubular member 38. Such a fluid access can be used to supply a measured amount of a fluid to an expansible balloon with a stent or other prosthesis located adjacent the distal end of the inner tubular member 24 as schematically indicated in FIGS. 1 and 2. A second port 70 can be located in front of the distal end cap 60 and seal 62 through which fluids can be introduced into the space 72 between the outer tubular member 32 and the intermediate tubular member 38. Fluids introduced through port 70 can flow toward the distal end 34 of the outer tubular member 32 outside the intermediate tubular member 38. The port 70 can also be used to withdraw a fluid initially situated in the vicinity of the outer tubular member distal end 34. The circumstances under which various fluids might be introduced or withdrawn through ports 66 and 70 will be apparent to those familiar with the general area of stent delivery catheter systems.

Figure 5:
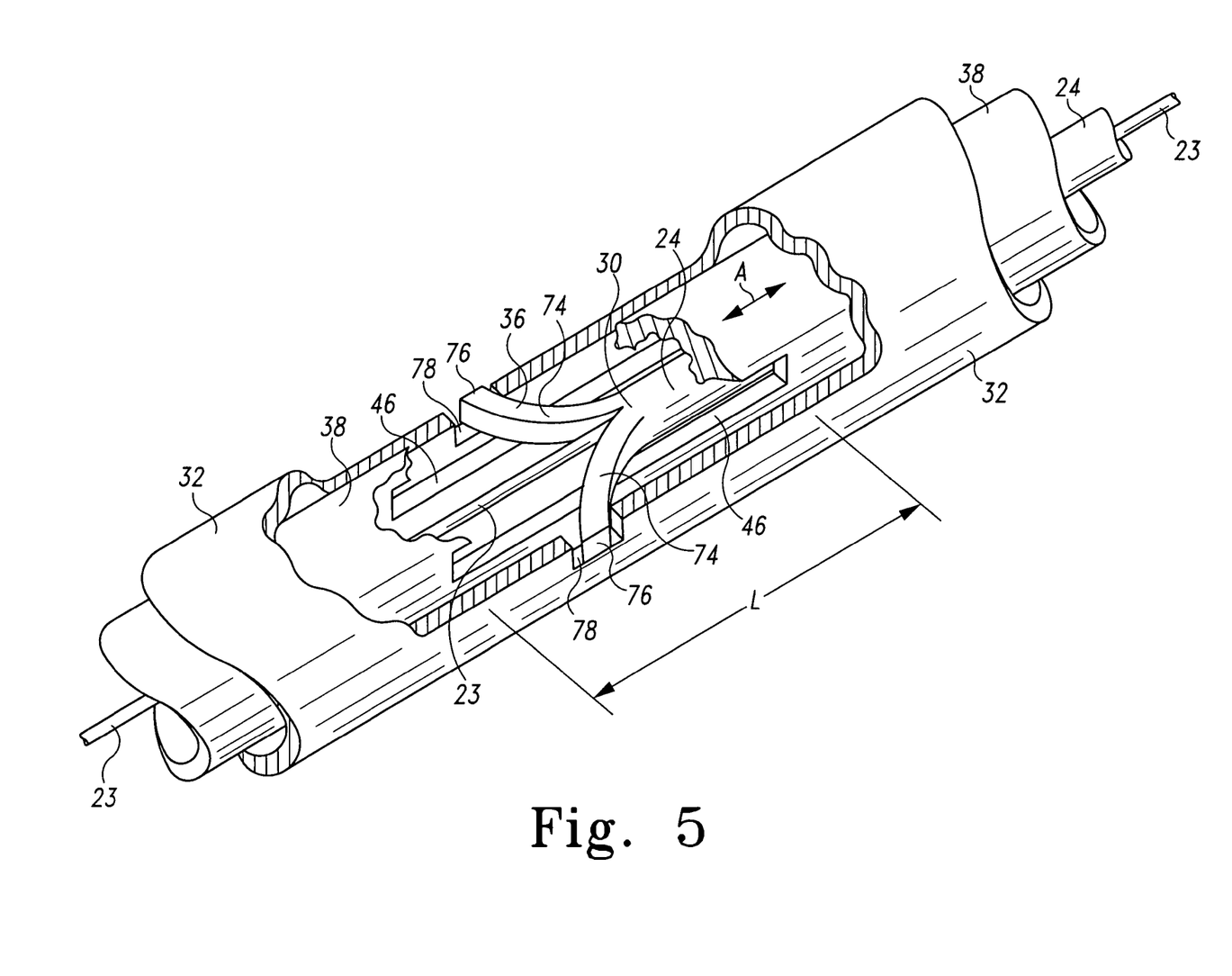
FIG. 5 is a perspective view partially broken away of the handle portion of a directional system of the present invention showing a connection yoke extending between the inner sheath and the handle through the slots in the cover sheath.

One embodiment of the handle portion 50 of the delivery system 20 is shown in FIG. 5 partially broken away to reveal more completely a coupling member 36 of the present invention. As in the previously described Figures, the coupling member 36 couples the inner tubular member 24 to the outer tubular member 32 to fix the positional relationship between the two members 24 and 32. The coupling member 36 is shown to take the form of curved diverging beams 74 splaying outward from the proximal end 30 of the inner tubular member 24. The curved diverging beams 74 forming the coupling member 36 pass through the slots 46 in the intermediate tubular member 38. Each diverging beam 74 has an outer end 76 that is received in a recess 78 in the outer tubular member 32. The outer ends 76 can be bonded, cemented, or otherwise secured to the recesses 78. The intermediate tubular member 38 is designed to be longitudinally moved in the direction of arrow A by a distance sufficient to retract the distal end 40 from any position covering the prosthesis 22 carried by the projecting portion 28 of the inner member 24, thus permitting the prosthesis 22 to expand as shown in FIG. 2. The length L of the slots 46 in relation to the size of the beams 74 forming the coupling member 36 can be used to regulate the length of longitudinal movement of the intermediate tubular member 38.

Figure 6:
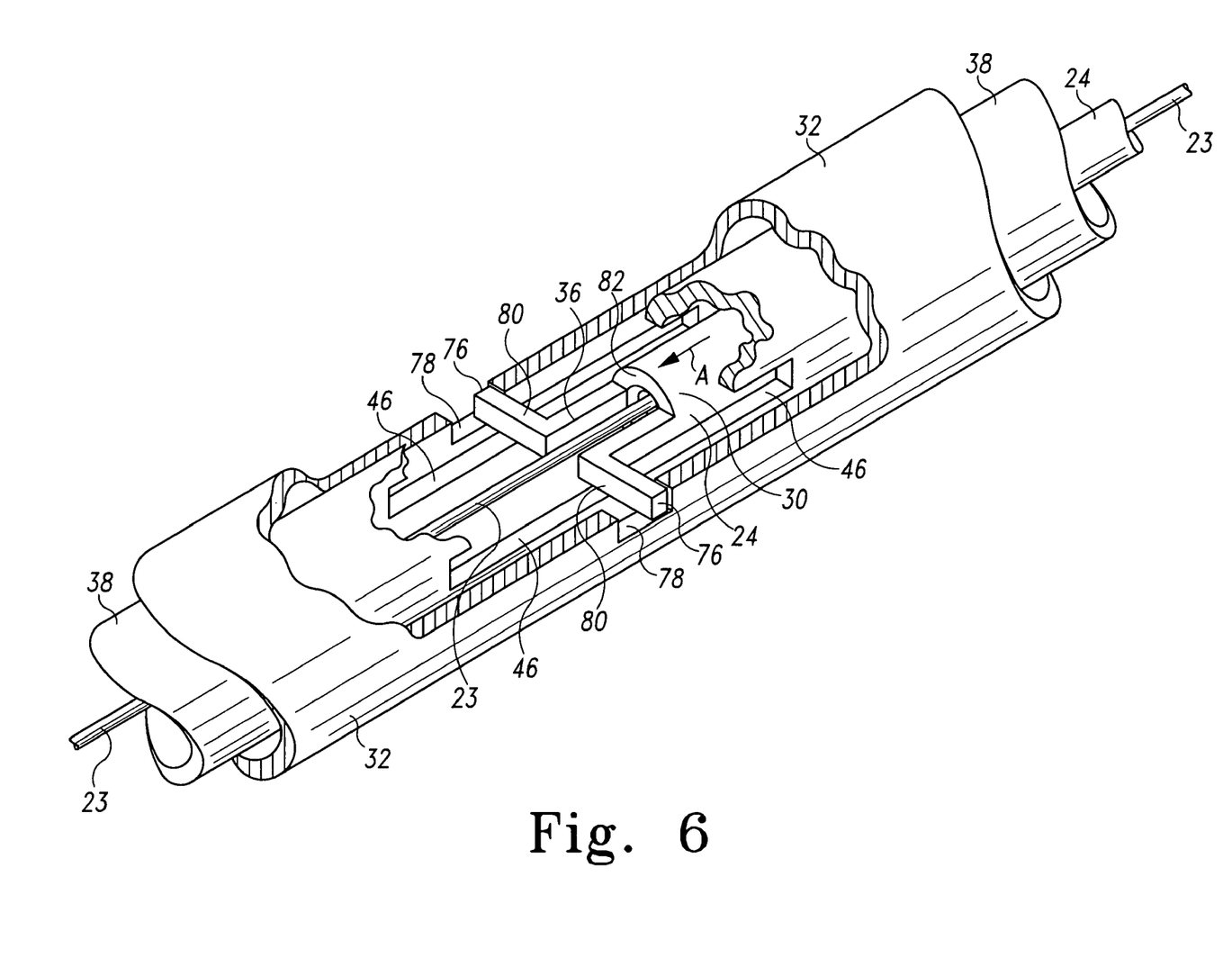
FIG. 6 is a perspective similar to FIG. 5 of another directional system of the present invention showing a different connection yoke extending between the inner sheath and the handle through the slots in the cover sheath.

Another embodiment of the handle portion 50 of the delivery system 20 is shown in FIG. 6 illustrating an alternative structure for the coupling member 36 of the present invention. As in FIG. 5, the coupling member 36 couples the inner tubular member 24 to the outer tubular member 32 to fix the positional relationship between the two members 24 and 32. The coupling member 36 is shown to take the form of two beams 80 extending radially outward from the proximal end 30 of the inner tubular member 24. The radially extending beams 80 forming the coupling member 36 pass through the slots 46 in the intermediate tubular member 38. Each radially extending beam 80 has an outer end 76 that is received in a recess 78 in the outer tubular member 32. The outer ends 76 of the beams 80 can be bonded, cemented, or otherwise secured to the recesses 78. The intermediate tubular member 38 is designed to be longitudinally moved in the direction A by a distance, which can be regulated by the length of the slots 46, sufficient to retract the proximal end 40 from any position covering the prosthesis 22 carried by the projecting portion 28 of the inner member 24, thus permitting the prosthesis 22 to expand as shown in FIG. 2. The proximal end 30 of the inner tubular member 24 can include a coupling surface 82 permitting the addition of other elements, not shown, to provide, for example, a channel leading to the interior of the inner tubular member 24.

Figure 7:
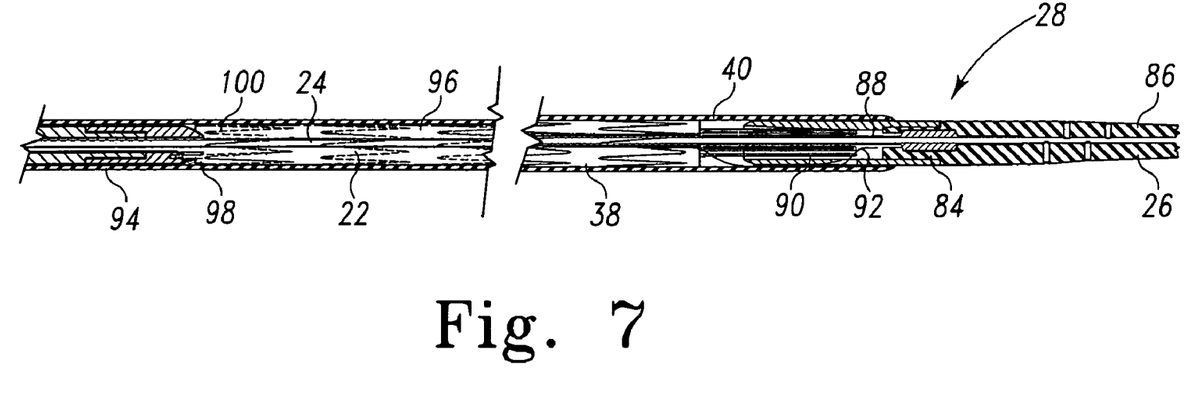
FIG. 7 is a sectional view of a distal end of a prosthesis deployment system of the present invention in an insertion and location attitude with the prosthesis in a retained position.
Figure 8:
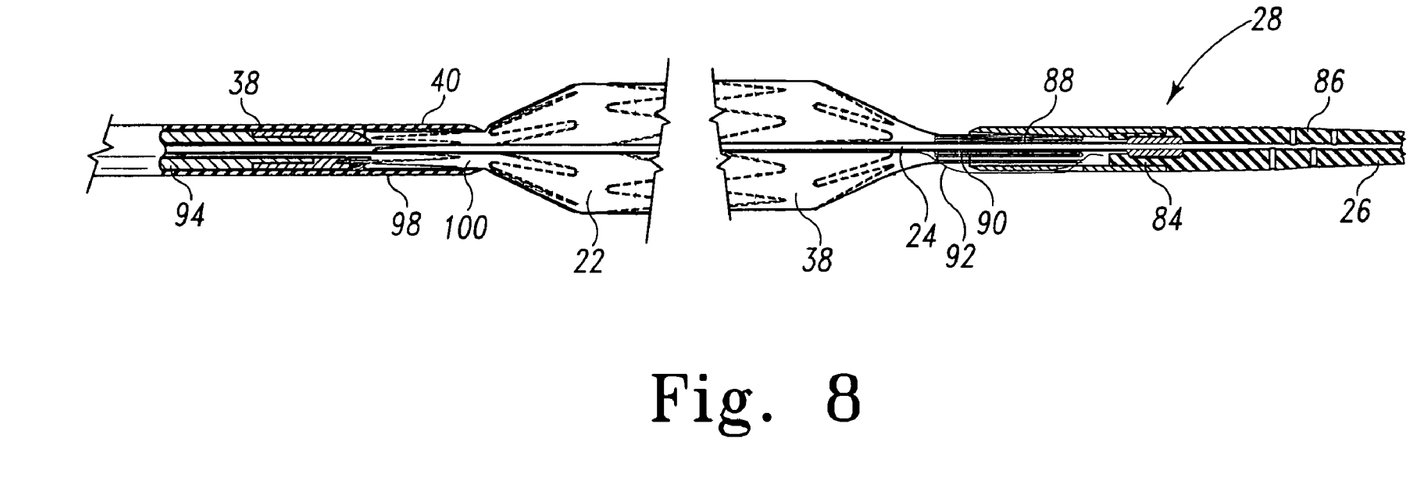
FIG. 8 is a sectional view similar to FIG. 7 showing the prosthesis partially deployed as a result of partial withdrawal of the cover sheath by movement of a handle such as that shown in one of FIGS. 3-6.

To better understand the operation of a delivery system 20 of the present invention, consider a distal end of the system 20 as shown in FIGS. 7 and 8 designed to deliver a self-expanding prosthesis 22. The projecting portion 28 of the inner member distal end 26 is seen to include an enlarged tip 84. The tip 84 has a tapered distal surface 86, which can extend a suitable distance to the right of FIG. 7. The tip 84 also includes a distal cavity 88. A distal portion 90 of the self-expanding prosthesis 22 is received in the proximal cavity 88. A trigger wire 92 secures the prosthesis distal portion 90 in the proximal cavity 88 until deployment. A ring member 94 is fixed to and surrounds the inner tubular member 24 at a position spaced from the tip 84. The space 96 between the ring member 94 and the tip 84 receives the prosthesis 22 in compressed condition prior to deployment. The distal end 40 of the intermediate tubular member 38 extends over the space 96 as shown in FIG. 7 to confine the prosthesis 22 in the space 96 prior to deployment. Another trigger wire 98 can retain the proximal end 100 of the prosthesis 22 to the ring member 94 until deployment. As viewed in FIG. 7, the distal end 34 of the outer tubular member 32 can be located at any position to the left of the space 96, and therefore is not shown. The distal end of the system 20 carrying the prosthesis 22 in compressed form as shown in FIG. 7 can be suitably positioned within a lumen of a patient using known procedures by movement of the handle portion 50 relative to the patient.

Figure 9:
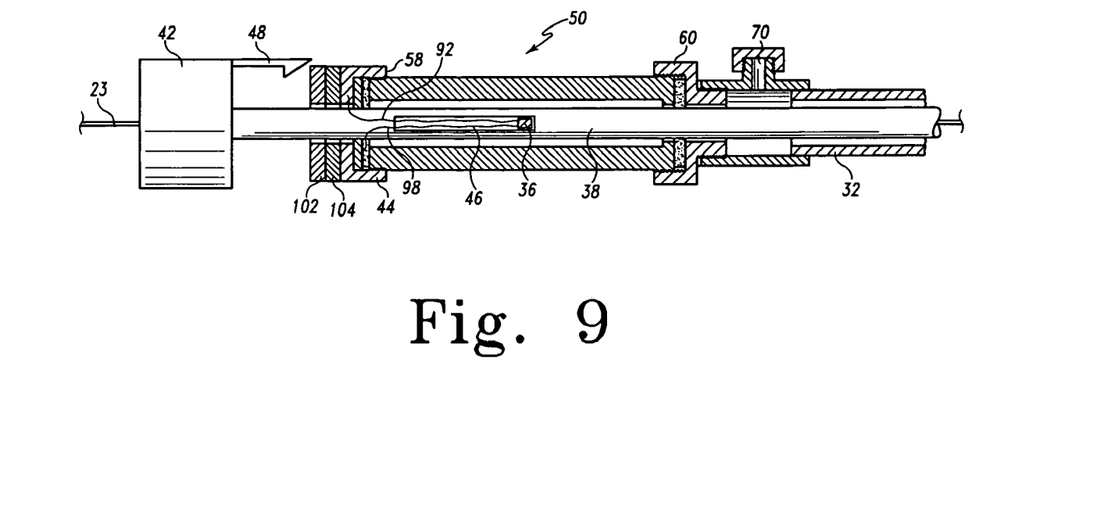
FIG. 9 is a sectional view similar to FIG. 4 wherein the sheath is retracted, but both ends of the stent are still connected to the inner catheter.
Figure 10:
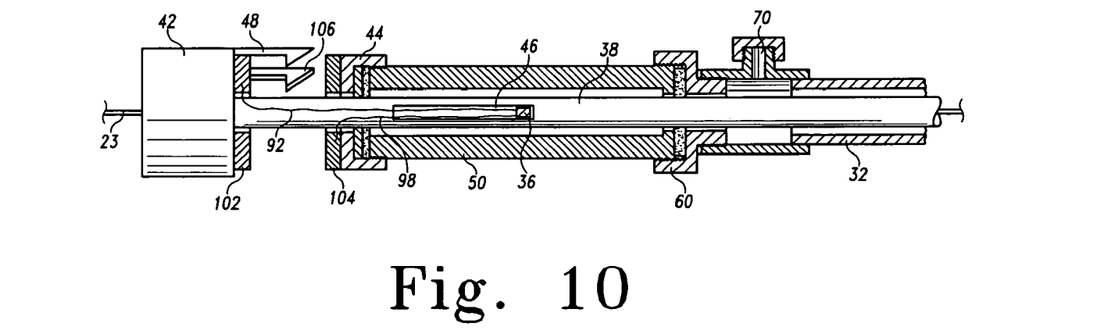
FIG. 10 is a section view similar to FIG. 9 wherein a first trigger wire release mechanism has been moved rearwardly to release a first end of the stent.
Figure 11:
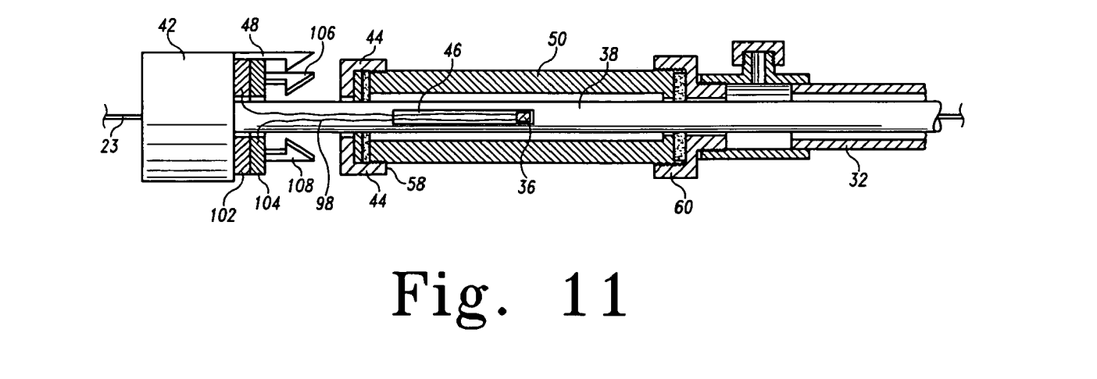
FIG. 11 is a section view similar to FIGS. 9 and 10 wherein a second trigger wire release mechanism has been moved rearwardly to release a second end of the stent, enabling withdrawal of the prosthesis deployment system.

The various elements of the delivery system 20 shown in FIGS. 7 and 8 can be manipulated with the present system 20 with a handle portion 50 as shown in FIGS. 9-11. The handle portion 50 is similar to that shown in FIG. 3 with the addition of two trigger wire pullers 102 and 104 that are situated between the enlarged distal end 42 of the intermediate tubular member 38 and the distal end cap 52. The trigger wire 92 can be coupled to the first trigger wire puller 102, and the trigger wire 98 can be coupled to the second trigger wire puller 104. The trigger wires 92 and 98 can extend from the trigger wire pullers 102 and 104 through slot 46 in the intermediate tubular member 38 to extend along the outside of the inner tubular member 24 to the locations shown in FIGS. 7 and 8. The trigger wire pullers 102 and 104 can each have latch mechanisms such as latches 106 and 108 shown in FIGS. 10 and 11 to prevent premature release of the associated trigger wires.

Subsequent to positioning the prosthesis 22 at a desired position within a patient, the deployment of the prosthesis 22 can achieved by releasing the latch 48 from the forward facing edge 58 of the proximal end cap 52 as described in connection with FIG. 3. With the latch 48 released, the enlarged proximal end 42 can be moved in the direction of arrow A until arriving at the position shown in FIG. 9. Such movement causes the distal end 40 of the intermediate tubular member 38 to move from the position extending over the space 96 as shown in FIG. 7 to the position shown in FIG. 8, thereby allowing the prosthesis 22 to expand outward toward contact of the wall of the surrounding lumen, not shown. Next, the latch 106 on the first trigger wire puller 102 is released and the puller 102 moved from the position shown in FIG. 9 to the position shown in FIG. 10. This action can release the trigger wire 92 from the tip 84 allowing the distal portion 90 of the prosthesis 22 to be released from cavity 88 to expand outward to engage the surrounding lumen wall. The latch 108 on the second trigger wire puller 104 can then be released and the second trigger wire puller 104 moved from the position shown in FIG. 10 to the position shown in FIG. 11. This action can release the trigger wire 98 from the proximal end 100 of the prosthesis 22 to permit expansion outward to engage the surrounding lumen wall. With the prosthesis 22 fully expanded, the delivery system 20 can then be withdrawn from the lumen.

Each of the elements 42, 102 and 104 can be independently latched to the handle 50 so that movement of the system 20 as a whole can easily place the prosthesis at the desired position within the patient. The order of manipulation of the various elements 42, 102 and 104 is in the same order as their location at the proximal end of the handle portion 50 of the system 20. Further, the deployment of the prosthesis is achieved by a simple rearward pulling movement of each of the elements. This ergonomic placement and operation is seen as aiding the physician in remembering the order of the movement of the various elements to achieve satisfactory placement of the prosthesis within the patient.

While various embodiments of the invention have been described, it will be apparent to those of ordinary skill in the art that many more embodiments and implementations are possible within the scope of the invention. Throughout this specification, unless the context requires otherwise, the words "comprise" and "include" and variations such as "comprising" and "including" will be understood to imply the inclusion of an item or group of items, but not the exclusion of any other item or group items. Furthermore, although various indications have been given as to the scope of this invention, the invention is not limited to any one of these but may reside in two or more of these combined together. Accordingly, the invention is not to be restricted except in light of the following claims and their equivalents.

The invention claimed is:

1. A delivery system for placement of a tubular prosthesis at a selected location within a lumen of a patient, the delivery system comprising:

an inner tubular member having a proximal end and a distal end, an outer tubular member having a proximal end and having a distal end spaced longitudinally some distance from the inner tubular member distal end so that a projecting portion of the inner tubular member projects distally beyond the outer tubular member distal end, the projecting portion being adapted to carry a tubular prosthesis, an intermediate tubular member having a proximal end projecting proximally beyond the proximal end of both the inner and outer tubular members, having a distal end adapted to cover at least the tubular prosthesis carrying portion of the inner tubular member, the intermediate tubular member having a longitudinal slot, and a coupling member comprising a protection extending outwardly from proximal end of the inner tubular member and extending through the longitudinal slot coupling the inner and outer tubular members to each other in permanent fixed relationship, the outwardly extending projection having an outer end coupled to the interior of the outer tubular member, the coupling member being longitudinally shorter than the longitudinal slot so that the intermediate tubular member is longitudinally movable with respect to the inner and outer tubular members, the longitudinal slot being sufficiently long to permit movement of the intermediate tubular member by a distance sufficient to retract the intermediate tubular member distal end from any position covering the tubular prosthesis carrying portion of the inner tubular member.

2. The delivery system of claim 1 wherein the longitudinal slot is situated in a proximal portion of the intermediate tubular member intended to remain outside the patient.

3. The delivery system of claim 1, wherein the intermediate tubular member includes a pair of said longitudinal slots and the coupling member comprises a pair of outwardly extending projections, wherein the outwardly extending projections are sufficiently flexible to permit inward radial collapse of the outer ends during initial assembly.

4. The delivery system of claim 3 wherein the outer tubular member further comprises a plurality of recesses sized to receive the outer ends of the outwardly extending projections.

5. The delivery system of claim 4 wherein the outer ends of the outwardly extending projections are secured in the recesses of the outer tubular member.

6. The delivery system of claim 1 wherein the outer tubular member comprises a proximal portion in the form of a handle including at least one port for admitting fluids into the interior of one or more of the tubular members.

7. The delivery system of claim 6 further comprising at least one release mechanism movably located at the proximal end of the outer tubular member to regulate the release of any tubular prosthesis.

8. The delivery system of claim 1, wherein the proximal end of the intermediate tubular member is enlarged to form a handle defining the most proximal portion of the system, wherein the handle is adapted to move proximally from the proximal end of the outer tubular member by a distance sufficient to retract the intermediate tubular member distal end from any position covering the tubular prosthesis carrying portion of the inner tubular member.

9. A method of placement of a tubular prosthesis at a selected location within a lumen of a patient, the method comprising the steps of:
providing a tubular prosthesis on a distal portion of an inner tubular member having a proximal end intended to remain outside said patient and a distal end,
locating coaxially an outer tubular member having a proximal end and a distal end so that the outer tubular member distal end is spaced longitudinally some distance from the inner tubular member distal end so that a projecting portion of the inner tubular member and the tubular prosthesis projects distally beyond the outer tubular member distal end,
locating an intermediate tubular member having a longitudinal slot between the inner and outer tubular members so that a distal end of the intermediate tubular member covers the prosthesis carried by the inner tubular member projecting portion and so that a proximal end of the intermediate tubular member projects proximally beyond the proximal end of both the inner and outer tubular members,
coupling the inner and outer tubular members to each other in permanent fixed relationship by a coupling member extending through the longitudinal slot in the intermediate tubular member, the coupling member comprising a projecting end extending outwardly from the proximal end of the inner tubular member through the longitudinal slot, wherein the outwardly project end is coupled to the interior of the outer tubular member,
positioning the prosthesis at a desired location within a patient, and
moving the proximal end of the intermediate tubular member with respect to the coupled inner and outer tubular members by a distance sufficient to retract the intermediate tubular member distal end from any position covering the prosthesis.

10. The method of claim 9 wherein the coupling of the inner and outer tubular members comprises the steps of:
providing a flexible portion of the inner tubular member with the outwardly projecting end,
displacing the flexible portion inward to permit the outwardly projecting end to pass within the intermediate tubular member until the outwardly projecting end is aligned with the longitudinal slot, and
allowing the flexible portion to flex outward through the longitudinal slot until the outwardly projecting end is received in a recess in the outer tubular member.

11. The method of claim 9 further comprising the steps of:
providing a latch to couple a proximal portion of the intermediate tubular member to the proximal end of the outer tubular member, and
releasing the latch prior to said step of moving the proximal end of the intermediate tubular member with respect to the coupled inner and outer tubular members.

12. The method of claim 9 or 11 further comprising the steps of:
providing at least one trigger wire extending from the prosthesis to the proximal end of the outer tubular member,
providing a trigger wire puller between the proximal end of the outer tubular member and the proximal end of the intermediate tubular member, and
moving the trigger wire puller proximally only after said step of moving the proximal end of the intermediate tubular member with respect to the coupled inner and outer tubular members.

13. The method of claim 12 further comprising the steps of:
providing a latch to couple the trigger wire puller to the proximal end of the outer tubular member, and
releasing the trigger wire latch only after said step of moving the proximal end of the intermediate tubular member with respect to the coupled inner and outer tubular members.

14. The method of claim 9 further comprising the steps of:
providing at least one port adjacent the proximal end of the outer tubular member,
coupling the at least one port to a source of fluid, and
causing a volume of fluid to flow from the source into one of the tubular members to assist in radial distension of the prosthesis.

15. A delivery system for placement of a tubular prosthesis at a selected location within a lumen of a patient, the delivery system comprising:
an inner tubular member having a proximal end and a distal end;
an outer tubular member having a proximal end spaced proximally beyond the inner tubular member proximal end and having a distal end spaced longitudinally some distance from the inner tubular member distal end so that a projecting portion of the inner tubular member projects distally beyond the outer tubular member distal end, the projecting portion being adapted to carry a tubular prosthesis;
an intermediate tubular member having an enlarged proximal end projecting proximally beyond the proximal end of both the inner and outer tubular members, and having a distal end adapted to cover at least the tubular prosthesis carrying portion of the inner tubular member, the intermediate tubular member having a longitudinal slot located distal to the proximal end of the outer tubular member, each of the tubular members having a coaxial relationship with one another; and a coupling member extending from the proximal end of the inner tubular member and through the longitudinal slot, to the interior of the outer tubular member, coupling the inner and outer tubular members in a permanent fixed relationship, the coupling member being longitudinally shorter than the longitudinal slot so that the enlarged proximal end of the intermediate tubular member is longitudinally movable with respect to the inner and outer tubular members, the longitudinal slot being dimensioned to permit movement of the intermediate tubular member by a distance sufficient to retract the intermediate tubular member distal end from any position covering the tubular prosthesis carrying portion of the inner tubular member.

16. The delivery system of claim 15, wherein the enlarged proximal end of the intermediate tubular member is movable between a first position and a second position relative to the coupled outer and inner tubular members, wherein at the first position the enlarged proximal end is adjacent the distal end of the outer tubular member, and at the second position the enlarged proximal end is longitudinally spaced from the distal end of the outer tubular member by a distance at least the length of the longitudinal slot.

17. The delivery system of claims 1 or 15, wherein the outer tubular member is coaxially disposed around the intermediate tubular member, surrounding the longitudinal slot of the intermediate tubular member so that the proximal end of the inner tubular member is located distally beyond the proximal end of both the intermediate and outer tubular members.

18. The delivery system of claim 15, wherein the enlarged proximal end of the intermediate tubular member further comprises a latch adapted to releasably couple said enlarged proximal end to a portion of the outer tubular member, the latch being releasable to permit movement of said enlarged proximal end relative to the coupled inner and outer tubular members.

19. The delivery system of claim 15 further comprising a handle on the outer tubular member proximal end including at least one seal contacting the intermediate tubular member to inhibit fluid leakage, and at least one port leading to the interior of the handle providing fluid access to the interior of at least one of the tubular members.

20. The delivery system of claim 6 or 19 wherein the handle further comprises a port leading to the interior of the handle to provide fluid access to the interior of the intermediate tubular member through said longitudinal slot.

21. The delivery system of claim 15 further comprising one or more pullers situated between the enlarged proximal end of the intermediate tubular member and the distal end of the outer tubular member, and one or more trigger wires corresponding to and coupled to the one or more pullers and extending through the longitudinal slot of the intermediate tubular member in order to releasably couple to one or more portions of said tubular prosthesis, the one or more pullers adapted to move proximally from the distal end of the outer tubular member after movement of the enlarged proximal end such that the one or more trigger wires is released from the tubular prosthesis, wherein the one or more pullers comprises a latch adapted to prevent premature release of the corresponding one or more trigger wires.

* * * * *

UNITED STATES PATENT AND TRADEMARK OFFICE
CERTIFICATE OF CORRECTION

| | | |
|---|---|---|
| PATENT NO. | : 7,691,139 B2 | |
| APPLICATION NO. | : 11/318690 | |
| DATED | : April 6, 2010 | |
| INVENTOR(S) | : Deborah A. Baker-Janis, James D. Purdy and Fred T. Parker | |

It is certified that error appears in the above-identified patent and that said Letters Patent is hereby corrected as shown below:

On the Title Page

Title Pg, under Item (12) delete "Baker et al." and insert --Baker-Janis et al.--.

Item (75) Inventors, first-named inventor should be listed as --Deborah A. Baker-Janis, Valencia, CA--.

In the Claims

In column 8, line 56, please delete "protection" and insert in lieu thereof --projection--.

Signed and Sealed this

Eighteenth Day of May, 2010

David J. Kappos
*Director of the United States Patent and Trademark Office*